(12) United States Patent
DiMarino et al.

(10) Patent No.: US 6,749,428 B2
(45) Date of Patent: Jun. 15, 2004

(54) DENTAL IMPRESSION TRAY

(75) Inventors: Jim DiMarino, Woodbury, NJ (US); Susan DiMarino, Woodbury, NJ (US)

(73) Assignee: Premier Dental Products Co., Plymouth Meeting, PA (US)

( * ) Notice: Subject to any disclaimer, the term of this patent is extended or adjusted under 35 U.S.C. 154(b) by 49 days.

(21) Appl. No.: 10/053,067

(22) Filed: Jan. 18, 2002

(65) Prior Publication Data

US 2003/0138754 A1 Jul. 24, 2003

(51) Int. Cl.[7] .................................................. A61C 9/00
(52) U.S. Cl. ........................................... 433/38; 433/37
(58) Field of Search ............................... 433/34, 37, 38, 433/41, 42, 43, 44, 45, 46, 47; D24/181

(56) References Cited

U.S. PATENT DOCUMENTS

| | | | | |
|---|---|---|---|---|
| 1,369,768 A | * | 3/1921 | Anderson | 433/37 |
| 4,204,323 A | * | 5/1980 | Neubert et al. | 433/38 |
| D266,269 S | | 9/1982 | Werrin | D24/10 |
| 4,668,188 A | * | 5/1987 | Wolfenson et al. | 433/37 |
| 4,689,010 A | | 8/1987 | Wolfe | 433/38 |
| 4,907,966 A | * | 3/1990 | Kesling | 433/37 |
| 5,316,474 A | | 5/1994 | Robertson | 433/38 |
| 5,636,985 A | | 6/1997 | Simmen et al. | 433/37 |
| D383,845 S | | 9/1997 | Mitchell et al. | D24/181 |
| 5,733,118 A | | 3/1998 | Pankuch et al. | 433/38 |
| D403,771 S | | 1/1999 | Werrin | D24/181 |
| 5,890,894 A | | 4/1999 | Mio et al. | 433/37 |
| 6,071,121 A | * | 6/2000 | Simon | 433/37 |

* cited by examiner

*Primary Examiner*—Cary E. O'Connor
(74) *Attorney, Agent, or Firm*—Drinker Biddle & Reath LLP (57) ABSTRACT

An improved dental impression tray provides an improved retentive force for the dental impression material contained therein by incorporating a plurality of projections and panels on its tray walls. Upon taking a dental impression, the dental impression material flows into the grooves defined by the plurality of projections, panels and the tray walls to form retentive components. These retentive components may prevent the impression material in the tray from distorting or being lifted out of the trays when the tray is disengaged from the oral anatomy of the patient.

13 Claims, 10 Drawing Sheets

DENTAL IMPRESSION TRAY

BACKGROUND OF THE INVENTION

1. Field of the Invention

This invention relates generally to a dental instrument and, more particularly, to trays for obtaining an impression of a patient's dentition.

2. Description of the Relevant Technology

Dental impression trays for obtaining an impression of a patient's dentition are known. Such trays generally include tray portions anatomically contoured to fit at least a part of a patient's upper and/or lower oral anatomy, of which an impression is to be obtained. There are mainly two techniques to taking dental impressions; the single arch and the closed bite technique. In the closed bite technique, the tray portion is loaded with a suitable dental impression material and situated over the part of the patient's oral anatomy of which an impression is desired. The patient then bites into the impression material to form an impression of the patient's oral anatomy in the impression material. After the impression material sets, it is used as a mold, into which plaster or dental stone can be poured which upon setting forms a model of the patient's oral anatomy. In addition, the set impression material may also be used directly as a mold for other purposes such as the fabrication of temporary restorations, the process of teeth whitening etc. A problem encountered in the use of conventional dental impression trays is that as and after the impression is taken and before and after the material sets, the impression material tends to move with respect to the wall or walls defining the tray portion. In particular, as the impression material starts to set while the impression is being taken, the soft impression material tends to separate from the wall and move inwardly into the tray portion and also tends to spread laterally along the wall. Moreover, after the impression is taken, the impression material tends to be lifted out and away from the dental impression tray walls as the patient's oral anatomy is removed from the impression material. Such a movement of the impression material distorts the impression obtained resulting in an ill-fitting dental product i.e. crown, bleaching tray, partial denture, restoration, etc.

Attempts have been made to prevent the soft impression material from moving in the manner described above. For example, sticky impression adhesives are available which are applied to the tray wall prior to the tray portion being loaded with impression material. However, the use of dental tray adhesives is not entirely satisfactory, as the distortion of the dental impression is not completely eliminated. Furthermore, the use of adhesives requires an additional step in the impression procedure and the application of adhesives to the dental tray is quite messy. In an impression tray available from Premier Dental Products, a corporation of Norristown Pa. and illustrated in U.S. Pat. No. Des. 266,269 and 277,605, a series of vertically extended ribs are formed in the tray wall, which at least to some extent inhibit lateral spreading of the impression material along the tray wall. However, the impression material still tends to separate from the wall and move inwardly into the tray as well as to be lifted out of the tray when the teeth are removed from the impression material.

U.S. Pat. No. 4,689,010 to Wolfe describes a dental impression tray which includes a tray portion anatomically contoured to fit over at least a part of the patient's upper and/or lower dentition of which an impression is to be obtained. The tray portion is defined by at least one wall, on which a plurality of vertically extending adjacent ribs are integrally formed defining a plurality of channels there between, into which the impression material flows. Each rib has a dovetail cross section so that the channels narrow or converge in the inward direction, i.e. towards the interior of the tray portion, to prevent the impression material from separating from the side wall in the inward direction as well as spreading laterally after the impression is taken. In this design each rib may be further provided with a lower surface situated within the tray portion and under which the impression material flows when the tray is loaded with impression material to prevent the impression material from being lifted out of the tray when the teeth are removed from the impression material. However the lower surface situated underneath each rib of Wolfe's dental impression tray makes it difficult to produce by common manufacturing techniques such as injection molding. In fact, U.S. Pat. No. 5,316,474 to Robertson tries to address some of the deficiencies in Wolfe's dental impression tray by providing a tray made with a low memory material.

Lastly, Wolfe's design cannot be used with a soft impression material such as alginate because the tray walls are too small to provide enough retention force to prevent the alginate impression material from distorting when the impression tray is being removed from the patient's mouth.

U.S. Pat. No. 5,733,118 to Pankuch et al. discloses a dental impression tray contoured to fit over at least a portion of a patient's dentition. The dental impression tray includes a first wall portion, a second wall portion substantially parallel with the first wall portion and an elongate rib to connect these two wall portions to form a channel between those two walls. Upon taking an impression of a patient's teeth, the impression material flows into the channel so that the impression material is more securely held in the tray upon its removal from the patient's teeth. However, this design suffers the similar drawback as the Wolfe's tray because it does not provide a 360° lock (locking the top, bottom, and both side edges of the wall) of the impression material by the tray walls. Instead it only provides an 180° lock (locking the top and bottom edges of the walls). In addition, for the material to be locked by the channels, the impression material has to overflow into the channel from the top of the walls. Therefore, the efficiency of forming a lock between the walls is dramatically decreased, especially for those quick setting materials. It has also been shown that this type of design is not suitable for the soft alginate dental impression materials because it does not provide enough retention force for these materials.

Currently, two of the most popular dental impression materials used by dental professionals are the vinyl polysiloxane (VPS) and the alginate-based impression materials. In fact dental professionals take millions of these types of impressions each year. Alginate is one of the most popular impression materials due to its accuracy, ease of removal from the teeth, inexpensive price, and ease of use. The VPS's are quite popular because they are extremely accurate, rigid, dimensionally stable, and give predictable results; although they are much more expensive. Therefore, a need exists to help dental health professionals to take these impressions using the most popular impression materials more conveniently.

Accordingly, it is an objective of certain embodiments of the present invention to provide a dental impression tray that provides enough retentive force for soft impression materials, such as alginate impression materials, upon taking a dental impression.

It is a second objective of certain embodiments of the present invention to provide a dental impression tray that provides more retentive force for the rigid, dimensionally stable impression materials, such as the vinylpolysiloxane impression materials.

It is a third objective of certain embodiments of the present invention to eliminate the need for adhesives for most impression materials by incorporating additional mechanical retention into a dental impression tray itself.

It is a fourth objective of certain embodiments of the present invention to provide a closed bite dental impression tray that can be easily removed from a patient's mouth after the impression has been taken by providing one or more perches points on the lateral aspect of the dental tray.

SUMMARY OF THE INVENTION

In a first aspect, the present invention provides a dental impression tray contoured to fit over at least a portion of a patient's oral anatomy. The dental impression tray includes cavity defining means including at least a first wall defining a receiving cavity for receiving an impression material; and a plurality of retaining elements that are structurally connected to the first wall, each of the retaining elements defining a parallel retention surface that is opposed to and substantially parallel to a portion of the first wall to which the retaining element is structurally connected, whereby the retaining elements will be positioned to effectively resist movement of the impression material in a direction that is perpendicular to the first wall during use.

In a second aspect, the present invention provides a method of obtaining a dental impression of a patient. The method includes the steps of filling a suitable amount of a dental impression material into a receiving cavity of a closed bite dental impression tray, properly placing the dental impression tray in a desired location inside the mouth of the patient and forming the impression after the patient bites into the dental impression material in the dental impression tray, wherein the dental impression tray includes cavity defining means including at least a first wall defining a receiving cavity for receiving an impression material; and a plurality of retaining elements that are structurally connected to the first wall, each of the retaining elements defining a parallel retention surface that is opposed to and substantially parallel to a portion of the first wall to which the retaining element is structurally connected, whereby the retaining elements will be positioned to effectively resist movement of the impression material in a direction that is perpendicular to the first wall during use.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENTS

Figure 1:
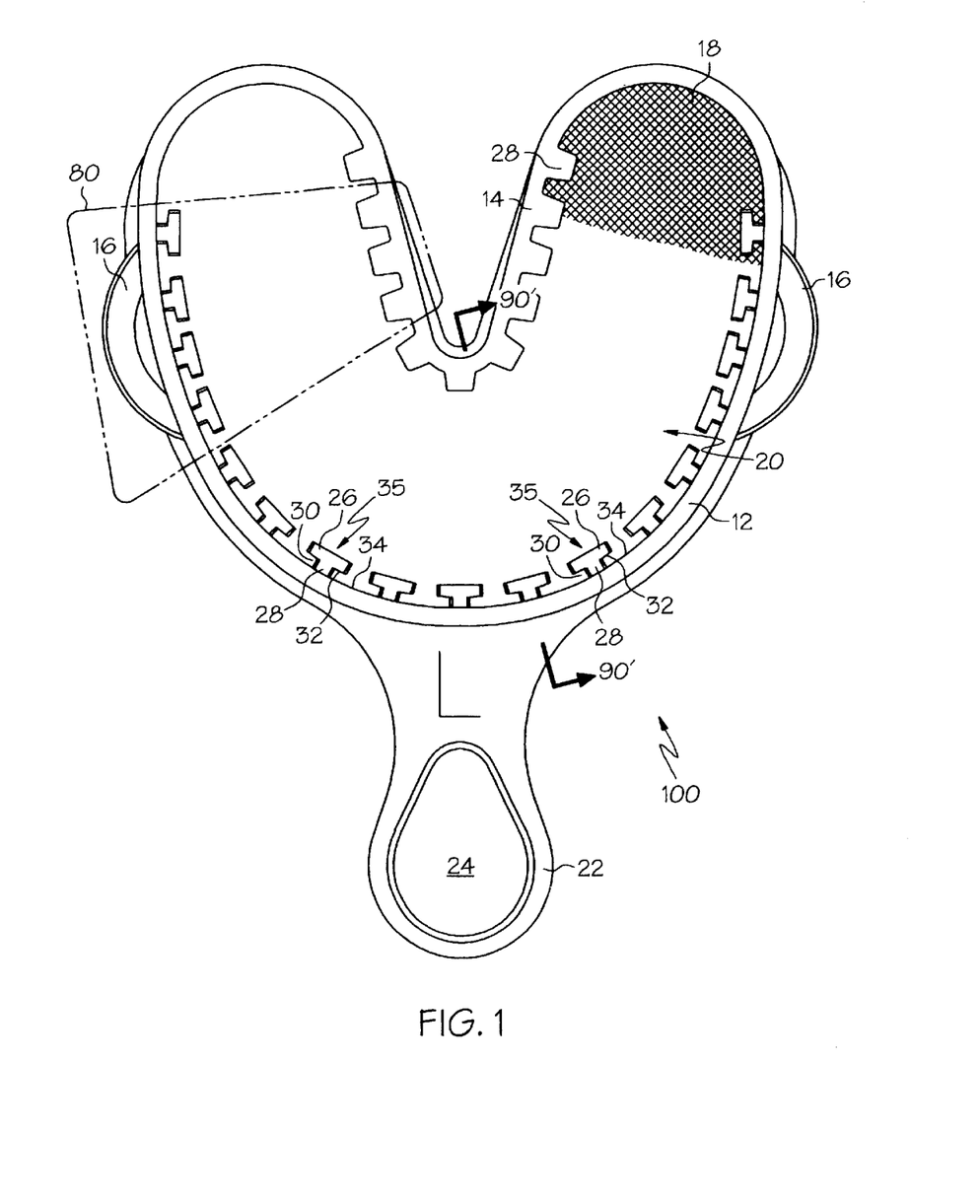
FIG. 1 is a top illustrative view of a dental impression tray according to the present invention.

Referring now to the drawings, wherein like reference numerals designate corresponding structures throughout the views, and referring in particular to FIG. 1, a dental impression tray 100 according to the present invention includes an outer wall 12 and an inner wall 14 connected at their ends together to define a receiving cavity 20 for receiving a dental impression material. The outer wall 12 and inner wall 14 may also be considered as a single close-ended wall to define the receiving cavity 20. Both the outer wall 12 and inner wall 14 are anatomically contoured in such a way that the formed tray fits at least a portion of a patient's oral anatomy such as the patient's dentition, gum, soft tissue in the vestibule or combination thereof. The tray 100 also includes a plurality of projections 28 structurally connected to the inner surface 34 of the outer wall 12. The tray further includes a plurality of panels 26, wherein each of the panels 26 is structurally connected to at least one of the projections 28 to form a retaining element 35. The panel 26 of each retaining element 35 has an inner surface 32, which is opposite to the inner surface 34 of the outer wall 12 and is substantially parallel with the portion of the outer wall 12, to which the retaining element 35 is structurally connected. Each panel 26 is located within the receiving cavity 20 defined by the outer wall 12 and the inner wall 14. Upon taking an impression, the inner surface 32 of each panel 26 serves as a retention surface for the impression material and prevents the impression material from being pulling away from the outer wall 12.

Preferably, both the outer wall 12 and inner wall 14 have a plurality of projections 28 connected thereto. Preferably, each projection 28 protrudes into the receiving cavity 20 from the corresponding walls 12 or 14, wherein the central axis of each projection 28 is substantially perpendicular to the portion of the walls 12 or 14, to which the projection 28 is structurally connected. The length of each projection 28 along its central axis is properly chosen so that the dental impression material held in the receiving cavity 20 can flow into the dental impression material retaining groove 30 between the outer wall 12 and panel 26, to both of which the projection 28 is structurally connected, to form a 360° lock.

The 360° lock formed therein may prevent the impression material from distorting or being pulled away from the outer wall 12. Preferably, the distance between the inner surface 32 of each panel 26 and the inner surface 34 of the outer wall 12 is between 0.025 inch and 0.075 inch.

Preferably, each panel 26 is elongated along a central axis, which is perpendicular to the central axis of the at least one projection 28, to which it is connected. More preferably, each panel 26 is substantially flat and substantially parallel to the portion of walls 12 or 14, to which it is connected through the at least one projection 28. The adjacent panels 26 along the outer wall 12 are properly spaced apart so that the dental impression material during an impression taking process can flow through the space between the adjacent panels 26 into the dental impression material retaining groove 30. Too little space may prevent or hinder the impression material from flowing into the groove 30. Too much space between the adjacent panels may reduce the retentive efficiency of the panels 26, as the total surface area of the inner surface 32 is inevitably reduced. Even more preferably, at least half of the outer wall 12 is covered by the plurality of panels 26. In a most preferred embodiment, the width of each panel 26, which is the dimension parallel with the plane defined by cavity 20 or partition 18, is between 0.1 inch and 0.5 inch, the height of each panel 26, which is the dimension perpendicular to the plane defined by receiving cavity 20 or partition 18, is between 0.1 inch and 1.0 inch.

In one preferred embodiment, there is not any panel 26 connected to the projections 28 protruding from the inner wall 14. In another preferred embodiment, a plurality of panels 26 are connected to the projections 28 protruding from the inner wall 14 and are properly spaced apart.

Preferably, the dental impression tray 100 further includes a handle 22, which may be contoured in shape to include a depression center 24 to accommodate a thumb. The handle 22 may be an extension of the outer wall 12. The tray 100 may further include a partition 18 attached at its edge marginal regions to the walls 12 and 14 halfway between the top and the bottom of the walls. The partition 18 separates the receiving cavity 20 defined by the walls 12 and 14 into a top portion and a bottom portion. The partition 18 may take the form of a paper, a meshwork such as a close mesh netting gauze, a thin membrane, other plastic or paper-like materials, or combination thereof. The impression tray 100 may further include one or more perch points 16 protruding from the outer wall 12. The one or more perch points 16 may receive the finger or fingers of a dental practitioner as they depress the perch points in order to disengage the dental impression tray 100 from the oral anatomy of a patient after a dental impression has been taken.

Figure 3:
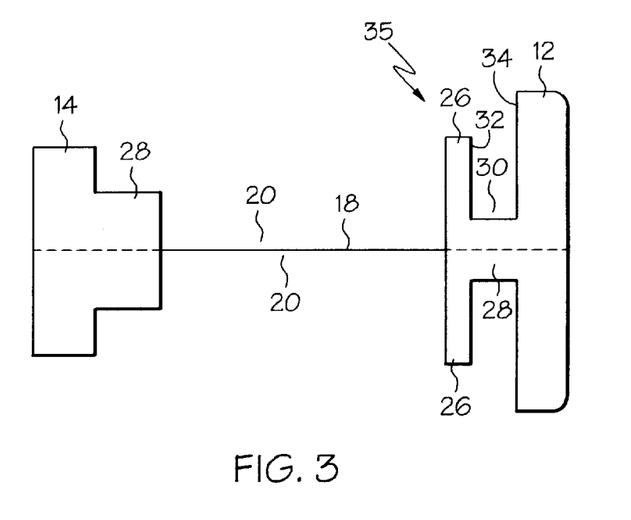
FIG. 3 is a cross sectional view of the tray walls as taken from line 90–90' of FIG. 1.

Preferably, at least one of the panels 26 is substantially longer than the corresponding at least one projection 28, to which it connects, in the direction perpendicular to the plane defined by the receiving cavity 20 or the partition 18 as shown in FIG. 3. More preferably, most of the panels 26 are substantially longer than their corresponding connected projections 28. Generally, each panel 26 is also substantially wider than its corresponding connected at least projection 28 in the direction parallel to the adjacent portion of the outer wall 12 and the partition 18 as shown in FIG. 1.

Figure 2:
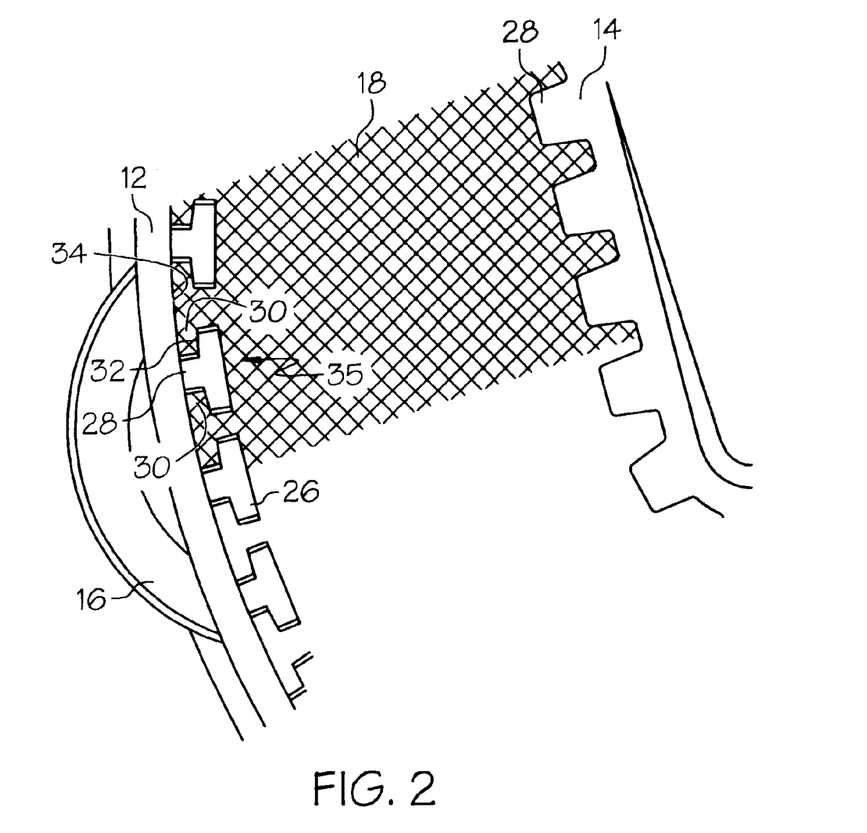
FIG. 2 is an enlarged view of portion 80 of the dental impression tray illustrated in FIG. 1.

FIG. 2, which is an enlarged view of section 80 of FIG. 1, further shows a panel 26, a projection 28 and the outer wall 12 together to define a dental impression material retaining groove 30, which can hold the overflowing impression material after the impression has been taken to hold the impression material to the wall 12.

FIG. 3 is a cross sectional view of the dental impression tray 100 of FIG. 1 along line 90–90'. The inner surface 32 of the panels 26 and the inner surface 34 of the outer wall 12 together with the corresponding projection 28 define a dental impression material retaining groove 30 there between. Upon taking the impression, some of the impression material flows into the groove 30 by going over the top of the panels 26 and through the space between the adjacent panels 26. The impression material in the groove 30 forms a 360° lock or retentive component. The impression material in the groove 30 locks the panel 26 from all sides of the panel 26 including top, bottom, left and right sides. The lock prevents the impression material in the receiving cavity 20 from being pulled away from the outer wall 12 when the impression material is removed from the teeth of a patient.

Figure 4:
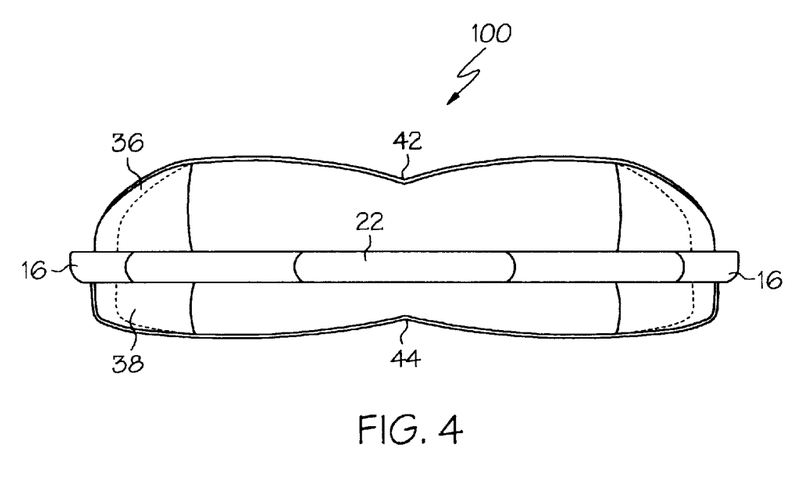
FIG. 4 is a front view of a dental impression tray according to a preferred embodiment of the present invention.

Referring now to FIG. 4, which is a front view of the dental impression tray 100 of the present invention, the outer wall 12 includes an upper portion 36 and a lower portion 38 that are separated by the handle 22 and the partition 18 (not shown in FIG. 4). The upper proportion 36 of the outer wall 12 of the dental tray 100 of the present invention has a notch 42 to accommodate a patient's maxillary frenum attachment. This notch may provide better patient comfort during the impression taking process. Similarly, a notch 44 is located at the lower portion 38 of the outer wall 12 to accommodate the mandibular frenum attachment of the patient.

Figure 5:
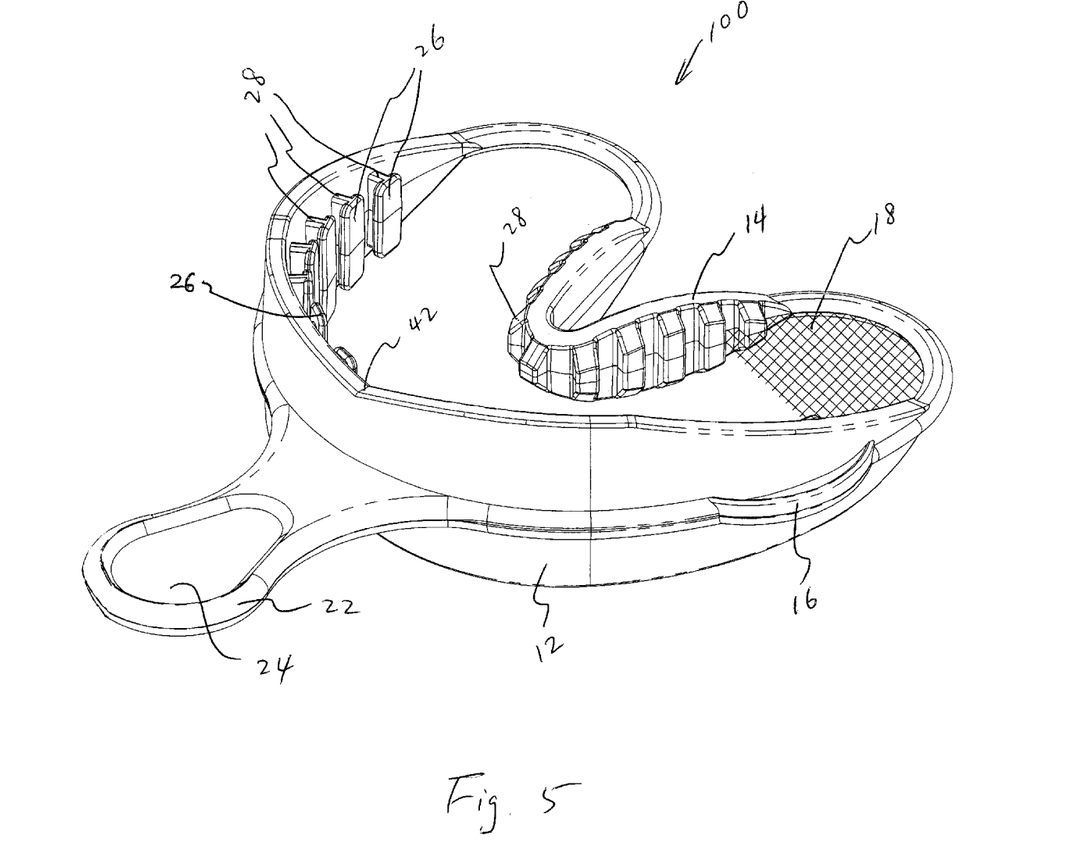
FIG. 5 is an elevated perspective view of a dental impression tray according to a preferred embodiment of the present invention.

FIG. 5 is an elevated perspective view of a preferred dental impression tray 100 of the present invention. The dental impression tray 100 includes a handle 22, with a depressed center 24, an outer wall 12 and an inner wall 14. The inner wall 14 and outer wall 12 are connected at their ends to define the dental impression material-receiving cavity 20. Both walls 12 and 14 have a plurality of projections 28 attached thereto. The outer walls 12 also have a plurality panels 26 attached thereto through the projections 28. The embodiment of FIG. 5 does not have any panel 26 attached to the inner wall 14 through projections 28. Optionally, the inner wall 14 may also have a plurality of panels 26 attached thereto via projections 28 in a similar way as the outer wall 12. Partition 18 is connected to both the inner wall 14 and outer wall 12 to separate the cavity 20 into a top portion and a bottom portion.

Figure 6:
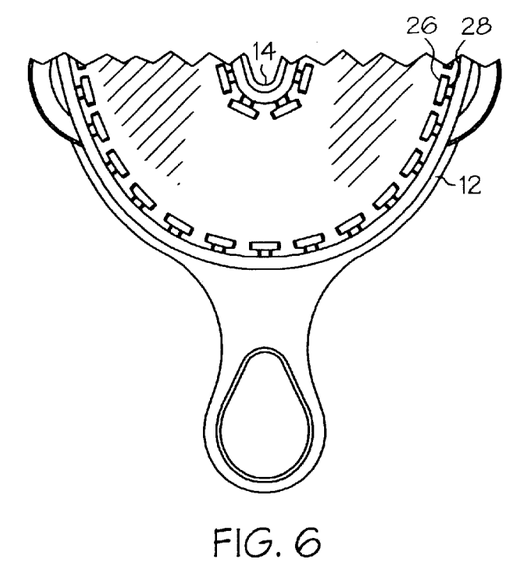
FIG. 6 is a top illustrative view of an anterior closed bite impression tray according to the present invention.
Figure 7:
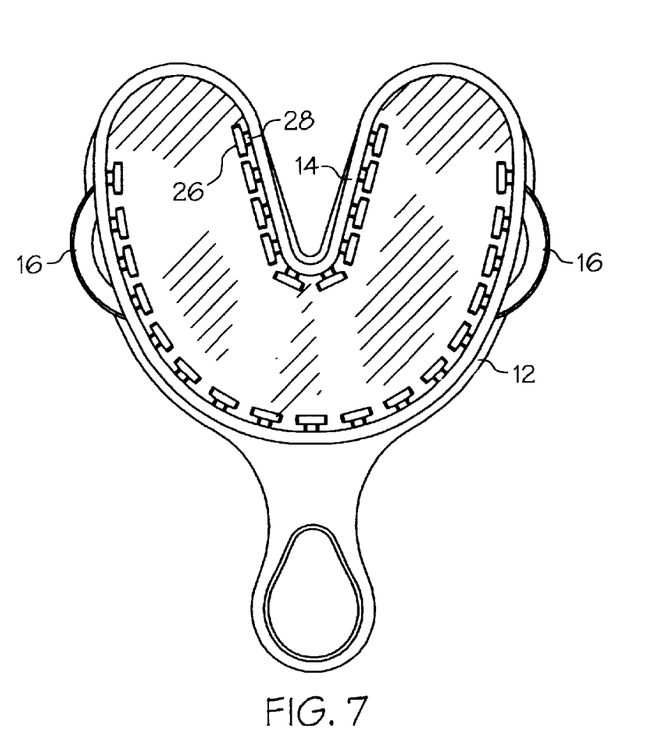
FIG. 7 is a top illustrative view of a three quarter arch closed bite impression tray according to a preferred embodiment of the present invention.
Figure 8:
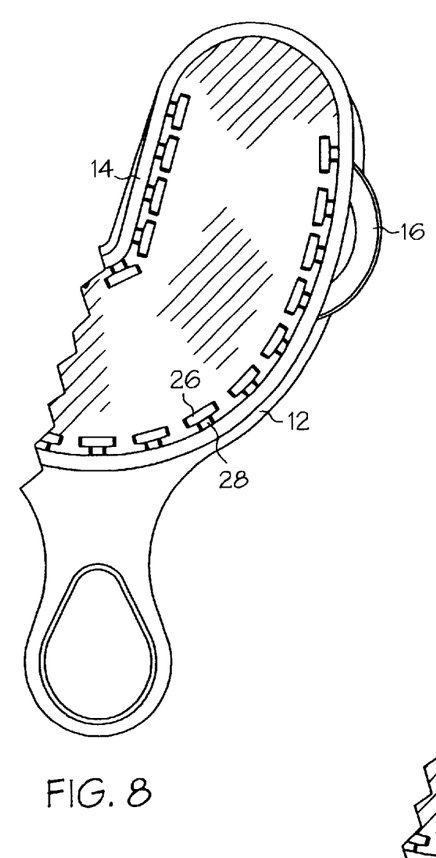
FIG. 8 is a top illustrative view of a posterior closed bite impression tray according to a preferred embodiment of the present invention.
Figure 9:
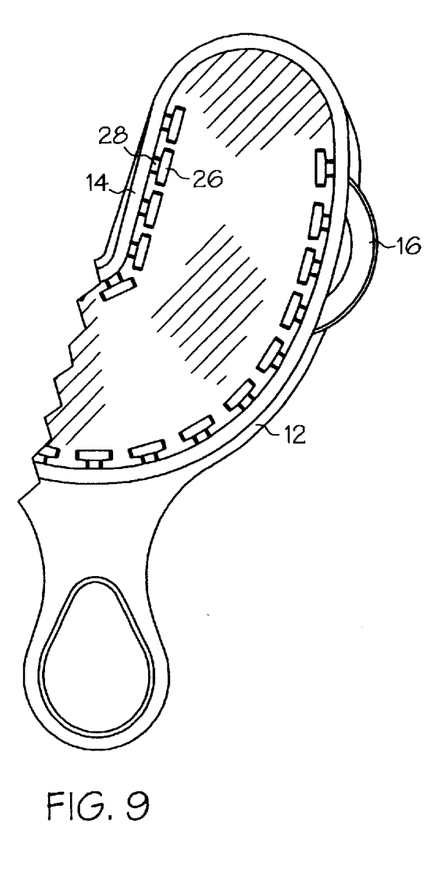
FIG. 9 is a top illustrative view of an extended quadrant closed bite impression tray according to a preferred embodiment of the present invention.

FIGS. 6 to 9 are top illustrative views of some of the other possible embodiments according to the present invention. FIG. 6 is a top illustrative view of an anterior closed bite impression tray according to the present invention including panels 26 and projections 28 on both of its outer wall 12 and inner wall 14. FIG. 7 is a top illustrative view of a three quarter arch closed bite impression tray according to the present invention. The dental impression tray of FIG. 7 includes a plurality of projections 28 and panels 26 connected thereto on both its inner wall 14 and outer wall 12. In addition, the dental impression tray of FIG. 7 further includes two perches points 16 on its outer wall 12. FIG. 8 is a top illustrative view of a posterior closed bite impression tray according to the present invention. The dental impression tray of FIG. 8 also includes an inner wall 14 and an outer wall 12. The dental impression tray of FIG. 8 further includes a plurality of panels 26 connected to walls 12 and 14 via a plurality of projections 28. In addition, the dental tray of FIG. 8 further includes a perches point 16 on its outer wall 12. FIG. 9 is a top illustrative view of an extended quadrant closed bite impression tray according to the present invention. The dental tray of FIG. 9 includes an outer wall 12, an inner wall 14 and a plurality of panels 26 and projections 28. Each panel 26 is connected to either wall 12 or wall 14 by a projection 28. In addition, the dental tray of FIG. 9 includes one perches point 16 on its outer wall 12. Many other variations are possible. For example, the dental tray many be sized to be a child size, small size, medium size, large size or extra size to fit a variety of oral anatomies.

Generally, the dental impression tray of the present invention is used to take an impression of a person's oral anatomy, which may be the person's dentition, gum, soft tissue in the vestibule, or combination thereof. The dental impression tray of the present invention may also be used to record a person's counter impression, bite registration or combination thereof. In a preferred embodiment, the dental impression tray is used to take an impression of a person's dentition.

Figure 10:
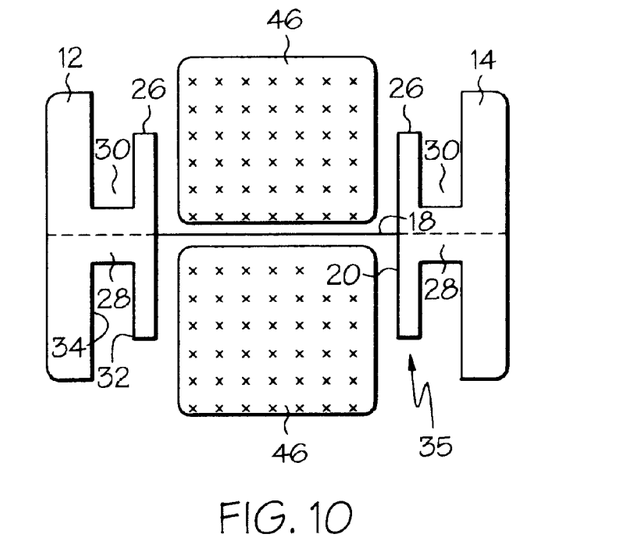
FIGS. 10 to 15 illustrate how a 360° lock or retentive force is achieved during a dental impression taking process using a dental impression tray of the present invention in a step-by-step process.
Figure 11:
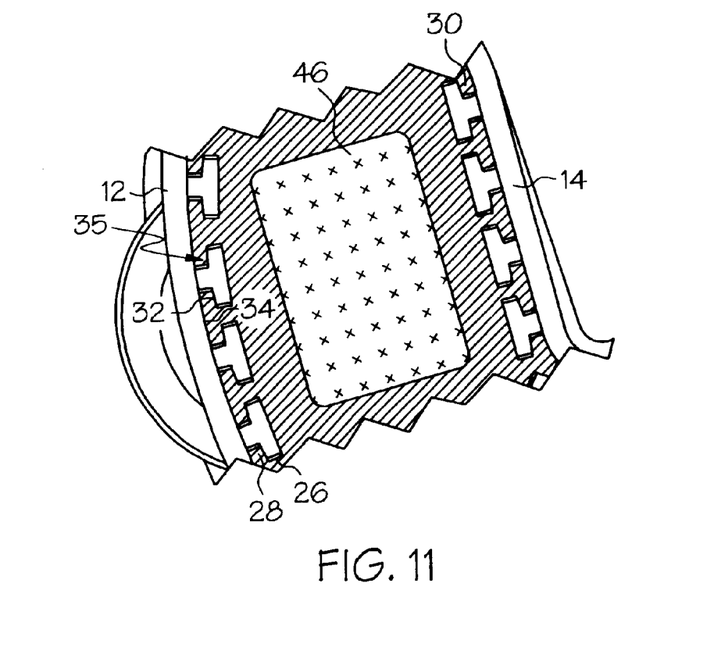
Figure 12:
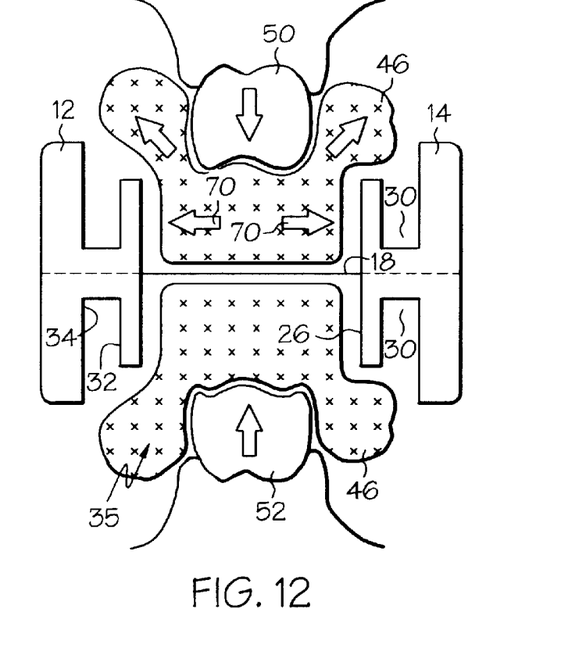
Figure 13:
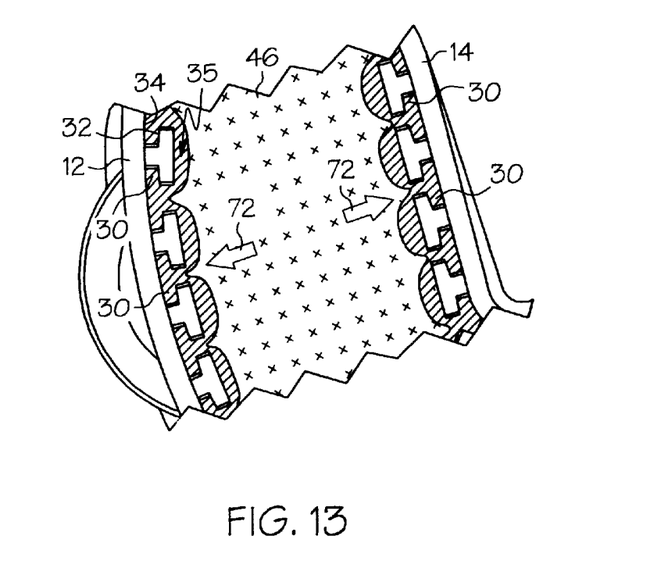
Figure 14:
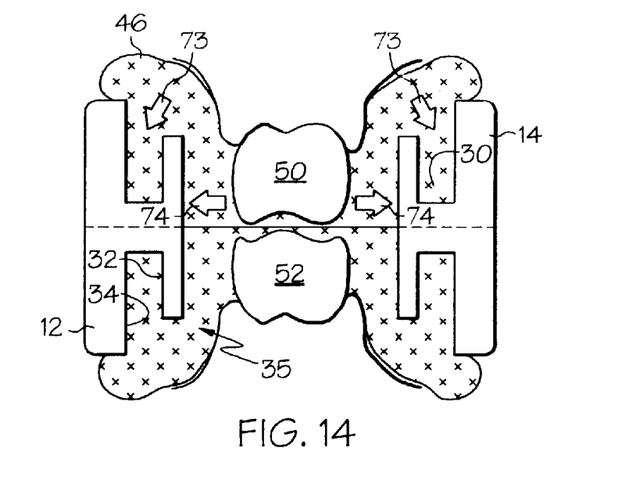
Figure 15:
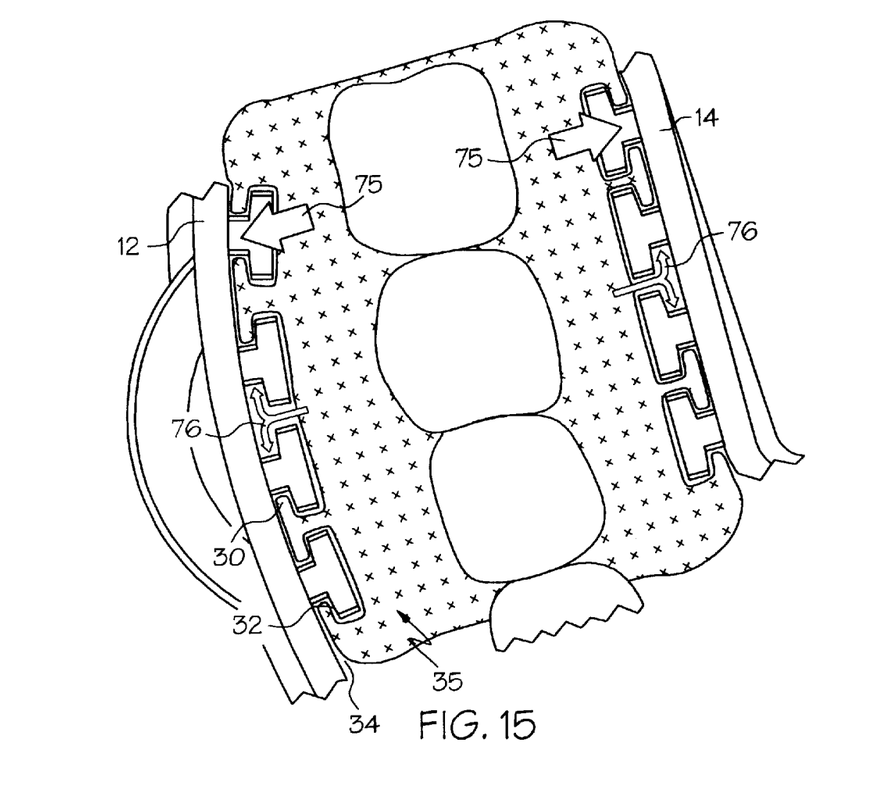

FIGS. 10 to 15 illustrate an impression material retention mechanism of a dental impression tray of the present invention. Even though the inventor does not want to be bound by the proposed mechanism here, the following description explains how the dental impression tray of the present invention may prevent the dental impression material from distorting and detaching from the dental tray walls when the impression material is removed from the teeth of a patient after the impression is taken. Referring now to FIG. 10, a cross sectional view of a dental impression tray of the present invention with dental impression material 46 filled in the cavity 20 defined by the wall 12, wall 14 and partition 18. FIG. 11 is a top view of the dental impression tray of FIG. 10 with the dental impression material 46 in place. Upon taking the impression by biting into the dental impression material with teeth 50 and 52 as shown in FIGS. 12 and 13. The soft dental impression material 46 overflows into the groove 30 defined by a panel 26, a projection 28 and the outer wall 12. By the same token, the soft dental impression material 46 may also flow into the groove 30 defined by a panel 26, a projection 28 and the inner wall 14. As the dental impression material 46 flows into the groove 30 as shown in FIGS. 12–15 (indicated by arrows 70, 72, 73, 74, 75 and 76), the dental impression material in the groove 30 forms a 360° lock to prevent the dental impression material from being detached from the outer wall 12 or inner wall 14 as been illustrated in FIGS. 14 and 15. Especially when the dental impression material 46 hardens gradually upon taking the impression before the dental impression is removed from the teeth of a patient, the impression material in the groove 30 may provide an additional lock or retentive force.

Figure 16:
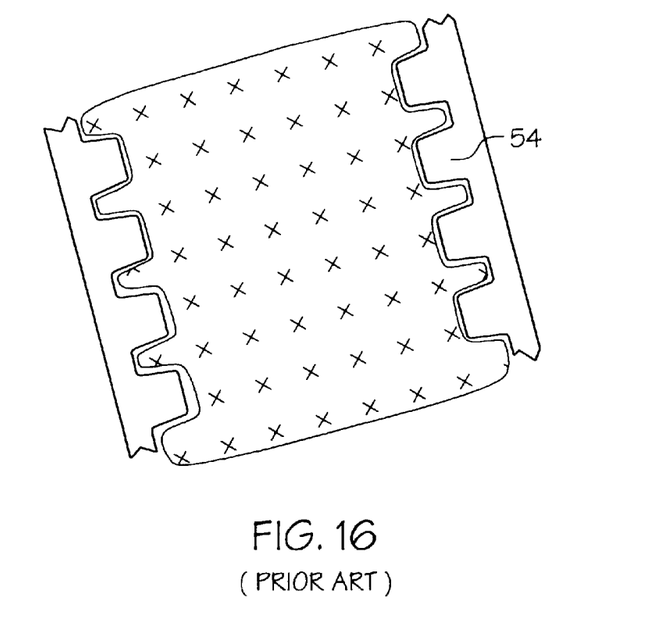
FIG. 16 is an example illustrating the lack of retentive force when a prior art dental tray is used.

This type of 360° lock formed by the dental impression material due to the presence of the panels 26 and projections 28, which together form T-shaped cross-sections when the dental impression tray is viewed from top as shown in FIG. 1, is more effective than the conventional locking mechanisms provided by a dovetail or simple rib 54 of a prior art dental impression tray as shown in FIG. 16. The type of 360° lock effectively resists the movement of the dental impression material 46 in the directions that are perpendicular or parallel to the walls 12 and/or 14. By using this T-shaped retentive mechanism of the preferred embodiment of the present invention, the retentive force of the walls 12 and 14 for the impression material is greatly improved over the prior art dental impression tray as shown in FIG. 16.

Figure 17:
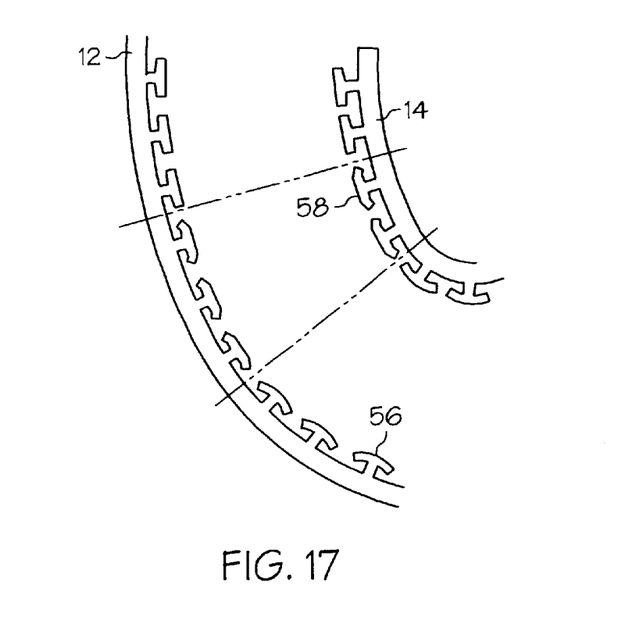
FIG. 17 illustrates some of the other possible variations of dental impression trays according to the present invention.

Other shapes of panels 26 and projections 28 may also be used in the present invention to form the 360° locking mechanism. For example, the panel 56 or 58 can be inwards C-shaped or beveled T-shaped as shown in FIG. 17 to provide an inward C-shaped or beveled T-shaped retaining surface opposite to the wall. Other variations of the retentive mechanism can be used without deviating from the 360° locking mechanism of the present invention. The preferred embodiment the dental impression tray of the present invention is particularly suitable for the alginate dental impression material because of its softness and proneness to be pulled out of the tray when used with the prior art dental impression trays.

The dental impression tray 100 of the present invention may be made from a suitable material such as plastics, metal and ceramic. In one preferred embodiment the dental tray 100 of the present invention may be made from a suitable plastic material such as polyvinyl chloride, nylon, and high-density polyethylene by injection molding. In fact, one advantage of the present invention is that the shape of the dental impression tray 100 of the present invention allows the dental impression tray to be manufactured by injection molding using common injection molding equipment to reduce the cost. Partition 18 may be made from a suitable mesh material or membrane material. Such mesh material may be selected from nylon, PVC and other suitable materials. Alternatively, partition 18 may be a membrane made from nylon, PVC and other suitable materials. In a more preferred embodiment the dental tray 100 of the present invention containing a partition 18 is made by a single step injection molding using high-density polyethylene. In such an embodiment, all the elements of the dental tray 100 including the walls, panels, projections, handle, perch points and the partition are unitary. In an alternative embodiment, the dental tray 100 of the present invention may be a reusable dental impression tray made from metal or any other suitable materials. Suitable materials for a reusable dental impression tray of the present invention include any sterilizeable materials such as stainless steel or other similar materials. In this embodiment, the partition 18 is preferably made from a sterilizeable or replaceable membrane.

The present invention provides an improved dental impression tray that prevents contraction of the impression material and holds the impression material more securely in the tray. In that regard, the present invention provides a dental impression tray with a plurality of projections and panels attached thereto to define grooves there between to provide a 360° locking mechanism or retentive force to hold the dental impression materials to the tray.

More specifically, the present invention provides a dental impression tray having a plurality of projections 28, a plurality of flat panels 26 connected to the projections and walls so that the dental impression material can flow behind the flat panels, and between the flat panels and the wall to form a strong 360° lock or retentive component to hold the dental impression material in place upon removal of the oral anatomy from the dental tray.

In a second aspect, the present invention provides a method of obtaining a dental impression of a patient. The method includes the steps of filling a suitable amount of a dental impression material into a receiving cavity of a dental impression tray of the present invention; properly placing the dental tray in a desired location inside the mouth of the patient; and forming the impression after the patient bites down the impression material in the dental impression tray.

In a preferred embodiment, the method of obtaining a dental impression may further involve the steps of letting the impression material harden in the tray for a suitable period of time after the patient bites down the impression material; and removing the dental impression tray from the mouth of the patient by pressing on the perches points of the dental impression tray. Generally, the dental impression tray of the present invention may be used with any impression material that is or will be available for recording the intra oral anatomy. In a more preferred embodiment, the dental impression material used in the method of the present invention is an alginate impression material.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

We claim:

1. A dental impression tray, comprising:
   means for defining a cavity including at least a first wall defining a receiving cavity for receiving an impression material;
   a plurality of retaining elements that are structurally connected to said first wall, each of said retaining elements defining a parallel retention surface that is opposed to and substantially parallel to a portion of said first wall to which said retaining element is structurally connected, whereby said retaining elements will be positioned to effectively resist movement of the impression material in a direction that is perpendicular to said first wall during use;
   each of said retaining elements comprising at least one projection that is connected to said portion of said first wall and a panel that is connected to said at least one projection, and wherein said parallel retention surface is defined by said panel.

2. A dental impression tray according to claim 1, further comprising a partition connected to the first wall, wherein said partition separates the receiving cavity into more than one portion, and wherein at least one of the panels is substantially longer than the at least one projection connected thereto in a vertical direction, the vertical direction being a direction substantially perpendicular to a plane defined by the partition.

3. A dental impression tray according to claim 1, wherein said plurality of retaining elements are properly spaced apart along said first wall, whereby the impression material will effectively flow into a groove defined by said retaining elements.

4. A dental impression tray according to claim 1, wherein said panel is unitary with said projection.

5. A dental impression tray according to claim 1, wherein said projection is elongated about a central axis, and wherein said central axis of said projection is substantially perpendicular to said portion of said first wall to which said retaining element is structurally connected.

6. A dental impression tray according to claim 5, wherein said panel is elongated about a central axis, and wherein said central axis of said panel is substantially perpendicular to said central axis of said projection.

7. A dental impression tray according to claim 1, wherein each of the panels together with the at least one projection connected thereto forms a T-shaped cross-section when viewed from top of the dental impression tray.

8. A dental impression tray according to claim 1, wherein said retaining element is unitary with said first wall.

9. A dental impression tray according to claim 1, wherein said means for defining a cavity further comprises a partition for separating the receiving cavity into more than one portion.

10. A dental impression tray according to claim 9, wherein said partition is fabricated from a mesh-material.

11. A dental impression tray according to claim 1, wherein said means for defining a cavity and said plurality of retaining elements comprise injection molded high-density polyethylene.

12. A dental impression tray, comprising:
    means for defining a cavity including at least a first wall defining a receiving cavity for receiving an impression material;
    said means for defining a cavity further comprising a second wall that is connected with said first wall and together with said first wall defines a receiving cavity for receiving an impression material;
    plurality of projections connected to the second wall;
    a plurality of retaining elements that are structurally connected to said first wall, each of said retaining elements defining a parallel retention surface that is opposed to and substantially parallel to a portion of said first wall to which said retaining element is structurally connected, whereby said retaining elements will be positioned to effectively resist movement of the impression material in a direction that is perpendicular to said first wall during use.

13. A dental impression tray according to claim 12, further comprising a plurality of panels connected to the second wall through the plurality of projections.

* * * * *